United States Patent [19]

Saxton et al.

[11] Patent Number: 5,618,512

[45] Date of Patent: Apr. 8, 1997

[54] NIOBIUM-CONTAINING ZEOLITES

[75] Inventors: Robert J. Saxton, West Chester; John G. Zajacek, Devon, both of Pa.

[73] Assignee: Arco Chemical Technology, L.P., Greenville, Del.

[21] Appl. No.: 565,711

[22] Filed: Nov. 30, 1995

[51] Int. Cl.$^6$ ............... C01B 39/08; C01B 39/40
[52] U.S. Cl. ............ 423/705; 423/713; 423/DIG. 22; 502/77
[58] Field of Search ................... 423/705, 713, 423/DIG. 22; 502/77

[56] References Cited

U.S. PATENT DOCUMENTS

| | | | |
|---|---|---|---|
| 3,702,886 | 11/1972 | Argauer et al. | 423/705 |
| 3,769,386 | 10/1973 | Rundell et al. | 423/713 |
| 4,371,457 | 2/1983 | Chu | 585/467 |
| 4,410,501 | 10/1983 | Taramasso et al. | 423/705 |
| 4,564,511 | 1/1986 | Desmond et al. | 502/77 |
| 4,576,805 | 3/1986 | Chang et al. | 423/DIG. 22 |
| 4,828,813 | 5/1989 | Moorehead | 423/713 |
| 5,354,719 | 10/1994 | Gabelica et al. | 502/77 |
| 5,518,707 | 5/1996 | Bedard et al. | 423/713 |

FOREIGN PATENT DOCUMENTS

| | | |
|---|---|---|
| 0178723 | 10/1985 | European Pat. Off. |
| 349115 | 12/1992 | Japan . |
| 9115426 | 10/1991 | WIPO . |

OTHER PUBLICATIONS

Lok et al. "The Role of Organic Molecules in Molecular Sieve Synthesis" *Zeolites* vol. 3 Oct. 1983 pp. 282–296.

*Handbook of Chemistry & Physics* Weast, Ed. 1971 pp. F-171–172.

"Synthetic & Mechanistic Aspects of Metal–Catalysed Epoxidations with Hydroperoxides", R. A. Sheldon, *Journal of Molecular Catalysis* 7 (1980) 107–126.

"Transition–Metal–Catalyzed Epoxidations", K. Jørgenson, *Chemical Reviews* 89, 3 (May 1989).

*Primary Examiner*—Karl Group
*Assistant Examiner*—David Sample
*Attorney, Agent, or Firm*—Stephen D. Harper

[57] ABSTRACT

Molecular sieve zeolites containing niobium isomorphously substituted in their framework lattice are obtained by hydrothermal crystallization using quaternary ammonium templates. The zeolites are useful catalysts, particularly for the oxidation of hydrocarbons such as olefins.

19 Claims, No Drawings

NIOBIUM-CONTAINING ZEOLITES

FIELD OF THE INVENTION

This invention relates to siliceous niobium-containing crystalline compositions wherein niobium is substituted in the framework of a microporous molecular sieve. The zeolites usefully catalyze the oxidation of organic substrates, including epoxidation of olefins using hydrogen peroxide.

BACKGROUND OF THE INVENTION

Zeolites are crystalline tectosilicates. Their structures typically consist of assemblies of $TO_4$ tetrahedra forming a three dimensional framework by sharing of the oxygen atoms. In zeolites of the aluminosilicate type, which are the most common, T represents tetravalent silicon as well as trivalent aluminum. The cavities and channels of this framework are of molecular dimension and collect cations, compensating the charge deficit associated with the presence of trivalent aluminum in the tetrahedra. Trivalent elements such as gallium or boron can be substituted for the aluminum.

In general, the composition of zeolites can be represented by the empirical formula $M_{2/n}O \cdot Y_2O_3 \cdot xZO_2$ in the dehydrated and calcined state. Z and Y respectively represent the tetravalent and trivalent elements of the $TO_4$ tetrahedra. Typically, Z is Si and Y is Al. M represents an electropositive element of valence n such as an alkali or alkaline earth metal, constituting the compensating cations. The value of x may range in theory from 2 to infinity, in which case the zeolite is a silica (silicalite).

Each type of zeolite has a distinct porous structure. Examples of types of zeolites having different three dimensional arrangements of their framework elements include ZSM-5 (MFI), zeolite beta, zeolite A, and so forth. The variation in pore size and shape from one type to another causes changes in the absorbent properties. Only molecules with certain sizes and shapes are capable of entering the pores of a particular zeolite. The chemical composition along with, in particular, the nature of the elements present in the $TO_4$ tetrahedra and the nature of the exchangeable compensating cations are also important factors affecting the absorptive selectivity and especially the catalytic properties of these products. Zeolites are consequently used as catalysts or catalyst supports in the cracking, reforming, and modification of hydrocarbons and the synthesis of various organic compounds.

For example, molecular sieves containing titaniun atoms isomorphously substituted for a portion of the silicon atoms in their framework lattice have in recent years been found to be highly active and useful catalysts for the epoxidation of olefins using hydrogen peroxide. See, for example, U.S. Pat. Nos. 4,833,260 and 5,453,511.

The substitution of different transition metals into the framework structures of molecular sieves is not straightforward, however, and often can only be successfully accomplished through very careful selection of reactants and reaction conditions. The preparation of transition metal-containing molecular sieves remains a highly uncertain and unpredictable art. For instance, while European Pat. Pub. No. 77,522 claimed the preparation of titano-aluminosilicates having a pentasil (ZSM-5) structure, later workers (Skeels et al., U.S. Pat. No. 5,098,687) demonstrated that the titanium atoms in the materials obtained were not actually present in the form of framework tetrahedral oxides.

To date, there have been few reports of niobium-containing molecular sieves in the literature. European Pat. Pub. No. 178,723 disclosed catalyst compositions for catalytic cracking of hydrocarbons comprised of porous matrix material containing crystalline aluminosolicates and a niobium component. However, it is clear from the description provided that the niobium in said catalyst compositions is merely impregnated or supported on the crystalline aluminosilicate and is not incorporated in the framework structure of the zeolite itself. Japanese Kokai JP 04-349,115 teaches crystalline silicates having the chemical composition in dehydrated form:

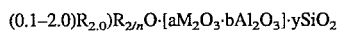

wherein R is $\geq 1$ monovalent or divalent ions, n is the valence of R, M can be Nb or another metal, $a+b=1, a>1$, $b \geq 0, y \geq 12$. Such materials thus must necessarily contain relatively high levels of exchangeable cations (e.g., alkali metal oxide or alkaline earth metal oxide cations). There is no suggestion that such crystalline silicates could effectively catalyze the epoxidation of olefins.

SUMMARY OF THE INVENTION

We have now unexpectedly discovered that it is possible to prepare a crystalline siliceous molecular sieve zeolite wherein niobium is isomorphously substituted for silica in the framework. In one embodiment of the invention, the zeolite has a silicalite (MFI) morphology. The framework niobium is retained during calcination. The calcined zeolite has been found to be active as an olefin epoxidation catalyst using aqueous hydrogen peroxide. This was quite surprising in view of the fact that although a number of different elements, including Al, Sn, V, Cr, Fe, Ga, and In have previously been reported to be isomorphously substituted in the framework of an all-silica ZSM-5, no metallosilicalite other than titanium silicalite has shown any significant epoxidation activity. Moreover, heterogeneous niobium compounds in general have heretofore been regarded as having little or no utility as olefin epoxidation catalysts. For instance, Sheldon [*J. Mol. Cat.* 7, 107–126 (1980)] reported that $Nb_2O_5$ gave only 9% t-butyl hydroperoxide conversion and 0% selectivity to 1-octene; oxide after 4.5 hours at 110° C. Only 5% epoxide selectivity was obtained using a niobium catalyst supported on silica.

DETAILED DESCRIPTION OF THE INVENTION

One objective of the present invention is to provide a new zeolite based on silica and niobium oxide.

Another objective of the invention is to synthesize the aforementioned zeolite according to a process wherein sources of silica and niobium oxide are combined and subjected to hydrothermal crystallization in the presence of a quaternary ammonium compound capable of acting as a template or structure directing agent. Such process incorporates niobium into the zeolite framework and leads to the production of microporous zeolite crystals in high yield having controlled pore dimensions and a high degree of crystallinity.

The zeolites of the present invention desirably correspond in their anhydrous calcined state to the following general formula (expressed in molar ratios):

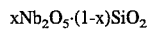

wherein x is from about 0.0005 to about 0.1. The Si/Nb molar ratio may thus be from about 4.5 to about 1000. Such zeolites are distinguishable from previously known niobium-containing molecular sieves by their low exchangeable cation levels. That is, the zeolites of the invention are characterized by the substantial absence of cations such as alkali metal and alkaline earth metal cations. In this context, "substantial absence" means that less than a total of 1000 ppm of such cations are present in the zeolite. The invention is capable of providing zeolites containing less than 100 ppm alkali metals and alkaline earth metals in total. In addition, little or no aluminum is present; the zeolites preferably contain less than 500 ppm Al. In a preferred embodiment of the invention, the zeolite comprises niobium in an amount effective to catalyze the epoxidation of olefins.

In a preferred embodiment of the invention, zeolites belonging to the pentasil family and having an MFI (ZSM-5) type structure are obtained. The zeolites have a crystallinity of at least 75%, as measured by XRD; the synthetic methods described herein are capable of providing crystallinities of 95% or greater. The zeolites of the present invention have a microporous structure and desirably have hexane adsorption values in the range of from about 0.17 to 0.20 cc/g.

If at least a portion of the niobium is incorporated into the lattice framework of the zeolite in the +5 oxidation state, the resulting positively changed framework may develop anion exchange capacity. Inorganic or organic anionic species can then be introduced into the zeolite by ion exchange. The identity and concentration of the anionic species may be manipulated so as to desirably alter the sorption capacity and catalytic activity of the zeolite.

Preferred methods for synthesizing the niobium-containing molecular sieves which are the subject of this application involve the use of a quaternary ammonium species. Without wishing to be bound by theory, it is believed that the quaternary ammonium species may function as a template for directing the assemblage of the required zeolite lattice framework from reactants which serve as sources of Si and Nb, but could also be accomplishing the desired synthetic result by acting as a buffer or structure-directing agent. The use of the term "template" herein is not meant to indicate that the quaternary ammonium species is in fact participating in a templating mechanism. The use of a quaternary ammonium species to prepare the catalysts of the present invention is advantageous since such a method tends to furnish molecular sieves which have low acidity, have little or no extra-framework Nb, and contain few defect sites.

Suitable quaternary ammonium species include, but are not limited to, compounds having the formula:

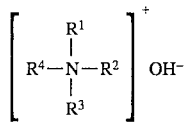

wherein $R^1$, $R^2$, $R^3$, and $R^4$ are the same or different and represent a linear or branched alkyl group with 1 to 6 carbon atoms. Preferably, the substituents on N are propyl or butyl groups. X may be halide or, more preferably, hydroxide. The most preferred quaternary ammonium species is tetrapropylammonium hydroxide. The morphology of the zeolite produced may be varied by the use of different quaternary ammonium species.

The niobium-containing molecular sieve of this invention may be prepared using the quaternary ammonium species in a solution-type synthesis. This method comprises forming a mixture, preferably in solution, of a hydrolyzable silicon compound, a hydrolyzable niobium compound, and the quaternary ammonium species, and subjecting said mixture to hydrothermal treatment at a temperature of from 100° to 200° C. (more preferably, 120° to 180° C.) for a time effective to form the crystalline niobium-containing molecular sieve. Such hydrothermal treatment is most preferably conducted in an aqueous medium (which may, in addition to water, contain a water-miscible organic solvent such as an alcohol) under conditions such that hydrolysis and/or mineralization of the silicon and niobium compounds is achieved. The process may be catalyzed by base, if so desired.

The hydrolyzable silicon compound may be any substance capable of functioning as a source of $SiO_2$ (silica) including, for example, amorphous or fumed silica or, more preferably, a tetraalkoxysilane such as tetraethyl orthosilicate or the like. Suitable hydrolyzable niobium compounds are those species which serve as a source of $Nb_2O_5$ (niobium oxide) such as niobium halide (e.g., $NbCl_5$) or, more preferably a niobium alkoxide such as niobium, isopropoxide or the like.

The starting reagents may, for example, may be selected to provide the following preferred molar ratios:

| | |
|---|---|
| $SiO_2/Nb_2O_5$ | 5–2000 |
| $OH^-/SiO_2$ | 0.1–2.0 |
| $H_2O/SiO_2$ | 20–200 |
| $Q^+/SiO_2$ | 0.1–2.0 | wherein Q is the cation associated with the quaternary ammonium species. A suitable preferred procedure for accomplishing formation of the mixture is as follows: partial hydrolysis of the hydrolyzable silicon compound is first carried out by reacting said compound with water containing a portion of the quaternary ammonium species (in hydroxide form). The partial hydrolysis product thereby obtained is then combined with the hydrolyzable niobium compound (and, optionally, an additional amount of the hydrolyzable silicon compound). The remaining amount of the quaternary ammonium species is thereafter added to yield a precursor gel or solution. Any volatile co-products generated as a result of hydrolysis (such as, for example, alcohols where the hydrolyzable silicon compound is a tetraalkyl orthosilicate or where the hydrolyzable niobium compound is a niobium alkoxide) may, if desired, be removed by any suitable means such as distillation or evaporation prior to hydrothermal treatment. The hydrothermal treatment is advantageously performed in an autoclave or other closed reactor under autogenous pressure. Typically, a period of from 3 to 20 days is sufficient to form the niobium-containing molecular sieve in crystalline, precipitated form. Such as-synthesized crystals, which will generally contain the quaternary ammonium species template, may be separated from the mother liquor by suitable means such as filtration, decantation, or centrifugation, washed with a suitable liquid medium such as water, then dried.

The crystalline product obtained by the above-described techniques may, if so desired, be calcined in air or the like at a temperature in excess of 400° C. in order to remove any template still present within the pores of the molecular sieve. The calcined molecular sieve may be contacted with hydrogen peroxide prior to use as a catalyst in order to increase its catalytic activity.

The niobium-containing molecular sieve of this invention may also be synthesized by adaptation of standard zeolite preparation techniques such as, for example, co-gel impregnation with template followed by hydrothermal treatment or dealumination of an aluminosilicate zeolite followed by reaction with a volatile niobium compound such as NbCl$_5$ to insert Nb into the framework vacancies created by dealumination.

In the epoxidation process of this invention, an olefin is contacted with hydrogen peroxide (or a substance capable of producing hydrogen peroxide under the reaction conditions) in the presence of a catalytically effective amount of the niobium-containing molecular sieve zeolite described hereinabove.

The amount of catalyst employed to epoxidize an olefin is not critical, but should be sufficient so as to substantially accomplish the desired reaction in a practicably short period of time. The optimum quantity of catalyst will depend upon a number of factors including reaction temperature, olefin reactivity and concentration, oxidizing agent concentration, type and concentration of organic solvent as well as catalyst activity. Typically, however, in a batch type epoxidation, the amount of catalyst will be from 0.001 to 10 grams per mole of olefin. In a fixed bed system, the optimum bed (typically, from about 1 to 100 moles oxidizing agent per kilogram of catalyst per hour). The concentration of niobium in the total epoxidation reaction mixture will generally be from about 10 to 10,000 ppm.

The catalyst may be utilized in powder, pellet, microspheric, monolithic, extruded, or any other suitable physical form. The use of a binder (co-gel) or support in combination with the niobium-containing molecular sieve may be advantageous. Supported or bound catalyst may be prepared by the methods known in the art to be effective for zeolite catalysts in general.

Illustrative binder and supports (which preferably are non-acidic in character) include silica, alumina, titania, silica-alumina, silica-titania, silica-thoria, silica-magnesia, silica-zironia, silica-beryllia, and ternary compositions of silica with other refractory oxides. Also useful are clays such as montmorillonites, kaolins, bentonites, halloysites, dickites, nacrites, and anaxites. The proportion of niobium-containing molecular sieve to binder or support may range from 99:1 to 1:99 but preferably is from 5:95 to 80:20.

The olefin substrate epoxidized in the process of this invention may be any organic compound having at least one ethylenically unsaturated functional group (i.e., a carbon-carbon double bond) and may be a cyclic, branched or straight chain olefin. The olefin may contain aryl groups (e.g., phenyl, naphthyl). Preferably, the olefin is aliphatic in character and contains from 2 to 30 carbon atoms (i.e., a $C_2$–$C_{30}$ olefin). The use of light (low-boiling) $C_2$ to $C_{10}$ mon-olefins is especially advantageous. More than one carbon-carbon double bond may be present in the olefin; dienes, trienes, and other polyunsaturated substrates thus may be used. The double bond may be in a terminal or internal position in the olefin or may alternatively form part of a cyclic structure (as in cyclohexene, for example). Other examples of suitable substrates include unsaturated fatty acids or fatty acid derivatives such as esters or glycerides and oligomeric or polymeric unsaturated compounds such as polybutadiene. Benzylic and styrenic olefins may also be epoxidized, although the epoxides of certain styrenic olefins such as styrene may further react or isomerize under the conditions utilized in the present invention to form aldehydes and the like.

The olefin may contain substituents other than hydrocarbon substituents such as halide, carboxylic acid, ether, hydroxy, thiol, nitro, cyano, ketone, acyl ester, anhydride, amino, and the like.

Exemplary olefins suitable for use in the process of this invention include ethylene, propylene, the butenes (e.g., 1,2-butene, 2,3-butene, isobutylene), butadiene, the pentenes, isoprene, 1-hexene, 3-hexene, 1-heptene, 1-octene, diisobutylene, 1-nonene, 1-tetradecene, pentamyrecene, camphene, 1-undecene, 1-dodecene, 1-tridecene, 1-tetradecene, 1-pentadecene, 1-hexaddecene, 1-heptadecene, 1-octadecene, 1-nonadecene, 1-eicosene, the trimers and tetramers of propylene, styrene (and other vinyl aromatic substrates) polybutadiene, polyisoprene, cyclopentene, cyclohexene, cycloheptene, cyclooctene, cyclooctadiene, cyclododecene, cyclododecetriene, dicyclopentadiene, methylenecyclopropane, methylenecyclopentane, methylenecyclohexane, vinyl cyclohexane, vinyl cyclohexene, methallyl ketone, allyl chloride, allyl bromide, acrylic acid, methacrylic acid, crotonic acid, vinyl acetic acid, crotyl chloride, methallyl chloride, the dichlorobutenes, allyl alcohol, allyl carbonate, allyl acetate, alkyl acrylates and methacryltaes, diallyl maleate, diallyl phthalate, unsaturated triglycerides such as soybean oil, and unsaturated fatty acids, such as oleic acid, linolenic acid, linoleic acid, erucic acid, palmitoleic acid, and riconoleic acid and their esters (including mono-, di-, and triglyceride esters) and the like.

Mixtures of olefins may be epoxidized and the resulting mixtures of epoxides either employed in mixed form or separated into the different component epoxides.

The process of this invention is especially useful for the epoxidation of $C_2$–$C_{30}$ olefins having the general structure

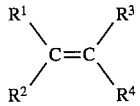

wherein $R^1$, $R^2$, $R^3$, and $R^4$ are the same or different and are selected from the group consisting of hydrogen and $C_1$–$C_{20}$ alkyl.

The oxidizing agent employed in the process of this invention may be a hydrogen peroxide source such as hydrogen peroxide ($H_2O_2$) or a compound which under the epoxidation reaction conditions is capable of generating or liberating hydrogen peroxide.

The amount of oxidizing agent relative to the amount of olefins not critical, but most suitably the molar ratio of oxidizing agent:olefin is from 100:1 to 1:100 when the olefin contains one ethylenically unsaturated group. The molar ratio of ethylenically unsaturated groups in the olefin substrate to oxidizing agent is more preferably in the range of from 1:10 to 10:1. One equivalent of oxidizing agent is theoretically required to oxidize one equivalent of a mono-unsaturated olefin substrate, but it may be desirable to employ an excess of one reactant to optimize selectivity to the epoxide.

Although the hydrogen peroxide which may be utilized as the oxidizing agent may be derived from any suitable source, a distinct practical advantage of the process of this invention is that the hydrogen peroxide may be obtained by contacting a secondary alcohol such as alpha-methyl benzyl alcohol, isopropyl alcohol, 2-butanol, or cyclohexanol with molecular oxygen under conditions effective to form an oxidant mixture comprised of secondary alcohol and hydrogen peroxide (and/or hydrogen peroxide precursors). Typically, such an oxidant mixture will also contain a ketone such as acetophenone, acetone, or cyclohexanone corresponding to the secondary alcohol (i.e., having the same carbon skeleton), minor amounts of water, and varying amounts of other active oxygen species such as organic hydroperoxides. Molecular oxygen oxidation of anthrahydroquinone, alkyl-substituted anthrahydroquinones, or water-soluble anthrahydroquinone species may also be employed to generate the hydrogen peroxide oxidant. The hydrogen peroxide may be generated in situ immediately prior to or simultaneous with epoxidation.

If desired, a solvent may additionally be present during the epoxidation process of this invention in order to dissolve the reactants other than the niobium-containing molecular sieve catalyst, to provide better temperature control, or to favorably influence the epoxidation rates and selectivities. The solvent, if present, may comprise from 1 to 99 weight percent of the total epoxidation reaction mixture and is preferably selected such that it is a liquid at the epoxidation reaction temperature. Organic compounds having boiling points at atmospheric pressure of from about 25° C. to 300° C. are generally preferred for use. Excess olefin may serve as a solvent or diluent. Illustrative example of other suitable solvents include, but are not limited to, ketones (e.g., acetone, methyl ethyl ketone, acetophenone), ethers (e.g., tetrahydrofuran, butyl ether), nitriles (e.g., acetonitrile), aliphatic and aromatic hydrocarbons, halogenated hydrocarbons, and alcohols (e.g., methanol, ethanol, isopropyl alcohol, t-butyl, alpha-methyl benzyl alcohol, cyclohexanol, trifluoroethanol). More than one type of solvent may be utilized. Water may also be employed as a solvent or diluent; surprisingly, the process of the invention proceeds with minimal hydrolysis even when a significant quantity of water is present in the epoxidation reaction mixture. Biphasic as well as monophasic reaction systems thus are possible using the present invention.

The reaction temperature is not critical, but should be sufficient to accomplish substantial conversion of the olefin to epoxide within a reasonably short period of time. It is generally advantageous to carry out the reaction to achieve as high a conversion of oxidizing agent as possible, preferably at least 50%, more preferably at least 90% most preferably at least 95%, consistent with reasonable selectivities. The optimum reaction temperature will be influenced by catalyst activity, olefin and oxidizing agent reactivity, reactant concentrations, and type of solvent employed, among other factors, but typically will be in a range of from about 0° C. to 150° C. (more preferably, from about 20° C. to 100° C). Reaction or residence times of from about 1 minute to 48 hours will typically be appropriate, depending upon the above-identified variables. Although subatmospheric pressures can be employed, the reaction is preferably (especially when the boiling point of the olefin is below the epoxidation reaction temperature) performed at atmospheric pressure or at elevated pressure (typically, between 1 and 100 atmospheres). Generally, it will be desirable to pressurize the epoxidation vessel sufficiently maintain the reaction the reaction components as a liquid phase mixture. For example, performing the epoxidation at elevated pressure will increase the solubility of gaseous reactants such as propylene in the solvent and oxidizing agent.

The process of this invention may be carried out in a batch, continuous, or semi-continuous manner using any appropriate type of reaction vessel or apparatus such as a fixed bed, transport bed, fluidized bed, stirred slurry, or CSTR reactor in a monophase or biphase system. Known methods for conducting metal-catalyzed epoxidations of olefins using an active oxygen oxidizing agent will generally also be suitable for use in this process. Thus, the reactants may be combined all at once or sequentially. For example, the oxidizing agent may be added incrementally to the reaction zone, the oxidizing agent could also be generated in situ within the same reactor zone where epoxidation is taking place. Once the epoxidation has been carried out to the desired degree of conversion, the epoxide product may be separated and recovered from the reaction mixture using any appropriate technique such as fractional distillation, extractive distillation, liquid-liquid extraction, crystallization, or the like. After separating from the epoxidation reaction mixture by any suitable method such as filtration, the recovered catalyst may be economically reused in subsequent epoxidations. Where the catalyst is deployed in the form of a fixed bed, the epoxidation product withdrawn as a stream from the epoxidation zone will be essentially catalyst free with the catalyst being retained within the epoxidation zone. In certain embodiments of the instant process where the epoxide is being produced on a continuous basis, it may be desirable to periodically or constantly regenerate all or a portion of the used niobium-containing molecular sieve catalyst in order to maintain optimum activity and selectivity. Suitable regeneration techniques include, for example, treating the catalyst with solvent and/or calcining the catalyst. Any unreacted olefin or oxidizing agent may be similarly separated and recycled. Alternatively, the unreacted oxidizing agent (especially if present at concentrations too low to permit economic recovery) could be thermally or chemically decomposed into non-peroxy species. In certain embodiments of the process where the oxidizing agent is hydrogen peroxide generated by molecular oxygen oxidation of a secondary alcohol, the crude epoxidation reaction mixture will also contain a secondary alcohol and ketone corresponding to the secondary alcohol. After separation of the epoxide from the secondary alcohol and the corresponding ketone, the ketone may be converted back to secondary alcohol by hydrogenation. For example, the ketone may be reacted with hydrogen in the presence of a transition metal hydrogenation catalyst. Hydrogenation reactions of this type are well known to those skilled in the art. The secondary alcohol may also be dehydrated using know methods to yield valuable alkenyl products such as styrene.

The niobium-containing molecular sieve described herein, in addition to being a useful epoxidation catalyst, also has utility as an ion exchanger, a shape-selective separation medium or a catalyst for other hydrocarbon conversion processes, including, for example: cracking, selectoforming, hydrogenation, dehydrogenation, oligomerization, alkylation, isomerization, dehydration, hydroxylation of olefins or aromatics, alkane oxidation, reforming, disproportionation, methanation, and the like. The molecular sieve of this invention is particularly useful for catalyzing the same reactions wherein titanium silicalites (also referred to as titanium silicates) have heretofore been employed. Illustrative applications of this type are as follows:

a) A process for the manufacture of a ketone oxime which comprises reacting a ketone such as cyclohexanone with ammonia and hydrogen peroxide in the liquid phase at a temperature of from 25° C. to 150° C. in the presence of a catalytically effective amount of the niobium-containing molecular sieve. Reactions of this general type are well known in the art and suitable conditions for carrying out such a synthetic transformation in the presence of a titanium silicalite catalyst are described, for example, in U.S. Pat. No. 4,745,221, Roffia et al., "Cyclohexanone Ammoximation: A Breakthrough in the 6-Caprolactam Production Process", in *New Developments in Selective Oxidation,* Centi et al, eds., pp. 43–52 (1990), Roffia et al., "A New Process for Cyclohexanonoxime", *La Chimica & L'Industria* 72, pp. 598–603 (1990), U.S. Pat. No. 4,894,478, U.S. Pat. No. 5,041,652, U.S. Pat. No. 4,794,198, Reddy et al., "Ammoximation of Cyclohexanone Over a Titanium Silicate Molecular Sieve", *J. Mol. Cat.* 69, 383–392 (1991), European Pat. Pub. No. 4.96,385, European Pat. Pub. No. 384,390, and U.S. Pat. No. 4,968,842, (the teachings of the foregoing publications are incorporated herein by reference in their entirety).

b) A process for oxidizing a paraffinic compound (i.e., a saturated hydrocarbon) comprising reacting the paraffinic compound at a temperature of from 25° C. to 200° C. with hydrogen peroxide in the presence of a catalytically effective amount of the niobium-containing molecular sieve. Reactions of this general type are well known in the art and suitable conditions for carrying out such a synthetic transformation in the presence of a titanium silicalite are described, for example, in Huybrechts et al., *Nature* 345,240 (1990), *Appl. Catal.* 68, 249 (1991), and Tatsumi et al., *J. Chem. Soc. Chem. Commun.* 476 (1990), Huybrechts et al., *Catalysis Letters* 8, 237–244 (1991 ), the teachings of which are incorporated herein by reference in their entirety.

c) A process for hydroxylating an aromatic hydrocarbon (e.g., phenol) comprising reacting the aromatic compound at a temperature of from 50° to 150° C. with hydrogen peroxide in the presence of a catalytically effective amount of the niobium-containing molecular sieve to form a phenolic compound (e.g., cresol). Reactions of this general type are well known in the art and suitable conditions for carrying out such a synthetic transformation in the presence of a titanium silicalite catalyst are described, for example, in U.S. Pat. No. 4,396,783, Romano et al., "Selective Oxidation with Ti-silicalite", *La Chimica L'Industria* 72, 610–616 (1990), Reddy et al., *Applied Catalysis* 58, L1–L4 (1990).

d) A process for isomerizing an aryl-substituted epoxide to the corresponding beta-phenyl aldehyde comprising contacting the aryl-substituted epoxide with a catalytically effective amount of the niobium-containing molecular sieve at a temperature of from 25° C. to 150° C. See, for example, U.S. Pat. No. 4,495,371 (incorporated herein by reference in its entirety).

e) A process for oxidizing a vinyl benzene compound to the corresponding beta-phenyl aldehyde comprising reacting the vinyl benzene compound with hydrogen peroxide at a temperature of from 20° C. to 150° C. in the presence of the niobium-containing molecular sieve. See, for an example of the use of titanium silicalite for such a transformation, U.S. Pat. No. 4,609,765 (incorporated herein by reference in its entirety).

f) A process for synthesizing an N, N-dialkyl hydroxylamine comprising reacting the corresponding secondary dialkyl amine with hydrogen peroxide in the presence of the niobium-containing molecular sieve. See, for an example of the use of titanium silicalite for such a transformation, U.S. Pat. No. 4,918,194 (incorporated herein by reference in its entirety).

g) A process for oxidizing an aliphatic alcohol comprising reacting the aliphatic alcohol with hydrogen peroxide in the presence of the niobium-containing molecular sieve at a temperature of from 25° C. to 150° C. to form the corresponding ketone or aldehyde of said aliphatic alcohol. See, for an example of the use of titanium silicalite for such a transformation, U.S. Pat. No. 4,480,135 (incorporated herein by reference in its entirety).

h) A process for synthesizing a glycol monoalkyl ether comprising reacting an olefin, an aliphatic alcohol, and hydrogen peroxide in the presence of the niobium-containing molecular sieve at a temperature of from 25° C. to 150° C. See, for an example of the use of titanium silicalite for such a transformation, U.S. Pat. No. 4,476, 327 (incorporated herein by reference in its entirety).

From the foregoing description, one skilled in the art can readily ascertain the essential characteristics of this invention, and, without departing from the spirit and scope thereof, can make various changes and modifications of the invention to adapt to its various usages, conditions, and embodiments.

EXAMPLES

A crystalline siliceous molecular sieve zeolite containing framework niobium in accordance with the present invention is prepared as follows. To a 250 mL plastic beaker was charged 40 g (0.192 mole)tetraethyl orthosilicate. To this was added dropwise 33.2 g of 40% aqueous tetrapropylammonium hydroxide solution (containing 0.065 mole TPAOH). The resulting clear solution was then stirred for one hour at room temperature. After this time, 6.27 g of a 10% niobium isopropoxide solution in isopropanol (containing 0.0016 mole niobium isopropoxide) was added dropwise. The solution, which remained clear, was stirred for an additional hour. After this time, an additional 4.2 g of 40% aqueous TPAOH was added (0.0083 mol TPAOH; 0.073 mole TPAOH total) together with 13 g deionized water. The solution was stirred one hour and then heated in a water bath at 70° C. with gentle nitrogen sparging to remove the alcohols. Over the course of one hour, an additional 14 g deionized water was added in aliquots. After this time the clear solution was loaded into a Teflon-lined Parr reactor and heated statically at 175° C. for 12 days. The white solids which formed were recovered by filtration, washed well with hot water, and dried at 120° C. overnight.

Powder x-ray diffraction analysis of the as-synthesized solids confirmed a crystalline MFI structure. The powder XRD spectrum was substantially identical to that of TS-1 titanium silicalite, except that the peaks were shifted to greater d-spacing as would be expected for a larger framework-substituted atom. The IR spectrum exhibited a peak at 952 $cm^{-1}$ having an intensity one-half that of the 800$cm^{-1}$ peak. Thermogravimetric analysis indicated that a 14% weight loss took place above 250° C., corresponding to the loss of the organic template initially trapped within the zeolite structure.

Calcination of the as-synthesized solids at 550° C. for 6 hours in dry air did not result in any significant loss of crystallinity (as measured by x-ray diffraction analysis). Elemental analysis of the calcined zeolite yielded the following results: 46% Si, 1.7% Nb, <100 ppm Al, corresponding to a Si/Nb molar ratio of 90. The hexane adsorption value was 0.183 cc/g, a void volume equivalent to that of TS-1 titanium silicalite and consistent with framework substitution of niobium in the silicalite.

The calcined niobium silicalite exhibited activity as a selective olefin epoxidation catalyst. After 3 days at room temperature, 1-hexene was epoxidized with aqueous hydrogen peroxide in acetonitrile (8 ml acetonitrile, 15 mmol olefin, 4.2 mmol $H_2O_2$, 0.15 catalyst)to 15% conversion and selectivity to epoxide of 95% based on hydrogen peroxide. No hexanediol or other by-products were observed, suggesting that niobium silicalite has little or no inherent Lewis or Bronsted acidity. In contrast, unnuetralized titanium silicalite (TS-1) typically produces significant amounts of glycol and/or glycol ether by-products under similar epoxidation conditions due to its higher acidity. After five days of reaction with the niobium silicalite, $H_2O_2$ conversion increased to 25%; epoxide selectivity remained >95%. This represents a total turnover number of about 40 based on niobium. Additional reaction time did not lead to conversions higher than 25%.

Initial activity was improved by first exposing the catalyst to hydrogen peroxide for 24 hours at 25° C. and then adding olefin. After 12 hours at room temperature under the same reaction conditions as described hereinabove, the hydrogen peroxide conversion was 11%. After 72 hours, the conversion had reached 76%. Epoxide selectivity had dropped to 32%, however, corresponding again to 40 total turnovers based on niobium.

We claim:

1. A method of making a crystalline siliceous molecular sieve zeolite having a zeolite framework structure isomorphous with ZSM-5, wherein niobium is substituted in said zeolite framework structure, and characterized by the substantial absence of exchangeable cations and aluminum, said method comprising:

(a) partially hydrolyzing a tetraalkoxysilane by reacting the tetraalkoxysilane with water containing a first portion of a quaternary ammonium species in hydroxide form to obtain a partial hydrolysis product;

(b) combining the partial hydrolysis product with a hydrolyzable niobium compound and a second portion of the quaternary ammonium species to yield a precursor product; and (c) subjecting the precursor product to hydrothermal treatment at a temperature of from 100° C. to 200° C. for a time effective to form as-synthesized crystals of the crystalline siliceous molecular sieve zeolite.

2. The method of claim 1 wherein the tetraalkoxysilane is tetraethyl orthosilicate.

3. The method of claim 1 wherein the hydrolyzable niobium compound is a niobium alkoxide.

4. The method of claim 1 wherein the quaternary ammonium species is tetrapropylammonium hydroxide.

5. The method of claim 1 wherein an additional portion of the tetraalkoxysilane is combined with the partial hydrolysis product in step (b).

6. The method of claim 1 wherein the precursor product comprises volatile alcohols, said volatile alcohols being removed from the precursor product prior to step (c).

7. The method of claim 1 wherein the tetraalkoxysilane, quaternary ammonium species, hydrolyzable niobium compound, and water are present in amounts sufficient to provide the following molar ratios:

| $SiO_2/Nb_2O_5$ | 5–2000 |
|---|---|
| $OH^-/SiO_2$ | 0.1–2.0 |
| $H_2O/SiO_2$ | 20–200 |
| $Q^+/SiO_2$ | 0.1–2.0 | wherein Q is the cation associated with the quaternary ammonium species.

8. The method of claim 1 comprising an additional step wherein the as-synthesized crystals are calcined.

9. The method of claim 1 wherein the as-synthesized crystals are calcined and subsequently contacted with hydrogen peroxide.

10. A method of making a crystalline siliceous molecular sieve zeolite having a zeolite framework structure isomorphous with ZSM-5, wherein niobium is substituted in the zeolite framework structure, and characterized by the substantial absence of exchangeable cations and aluminum, said method comprising (a) partially hydrolyzing a tetraalkoxysilane by reacting the tetraalkoxysilane with water containing a first portion of a quaternary ammonium species having the general structure

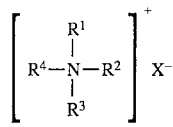

wherein $R^1$, $R^2$, $R^3$ and $R^4$ are the same or different and each represent a linear or branched alkyl group having 1 to 6 carbon atoms, to obtain a partial hydrolysis product;

(b) combining the partial hydrolysis product with a niobium alkoxide and a second portion of the quaternary ammonium species to yield a precursor product; and (c) subjecting the precursor product to hydrothermal treatment at a temperature of from 100° C. to 200° C. for a time effective to form as-synthesized crystals of the crystalline siliceous molecular sieve zeolite.

11. The method of claim 10 wherein the tetraalkoxysilane is tetraethyl orthosilicate.

12. The method of claim 10 wherein the niobium alkoxide is niobium isopropoxide.

13. The method of claim 10 wherein the quaternary ammonium species is tetrapropylammonium hydroxide.

14. The method of claim 10 wherein an additional portion of the tetraalkoxy silane is combined with the partial hydrolysis product in step (b).

15. The method of claim 10 wherein the precursor product comprises volatile alcohols, said volatile alcohols being removed from the precursor product prior to step (c).

16. The method of claim 10 wherein the tetraalkoxysilane, quaternary ammonium species, hydrolyzable niobium compound, and water are present in amounts sufficient to provide the following molar ratios:

| $SiO_2/Nb_2O_5$ | 5–2000 |
|---|---|
| $OH^-/SiO_2$ | 0.1–2.0 |
| $H_2O/SiO_2$ | 20–200 |
| $Q^+/SiO_2$ | 0.1–2.0 | wherein Q is the cation associated with the quaternary ammonium species.

17. The method of claim 10 comprising an additional step wherein the as-synthesized crystals are calcined.

18. The method of claim 10 wherein the as-synthesized crystals are calcined and subsequently contacted with hydrogen peroxide.

19. The method of claim 10 wherein the crystalline siliceous molecular sieve zeolite in an anhydrous calcined state corresponds to the general formula $$xNb_2O_5 \cdot (1-x)SiO_2$$

wherein x is from about 0.0005 to about 0.1.

* * * * *